United States Patent
Freer et al.

(10) Patent No.: US 8,831,711 B2
(45) Date of Patent: Sep. 9, 2014

(54) IMPLANTABLE CARDIAC SYSTEMS WITH BASELINE CORRECTION IN RESPONSE TO NOISE DETECTION

(71) Applicant: Cameron Health, Inc., San Clemente, CA (US)

(72) Inventors: Paul Freer, Anaheim, CA (US); Rick Sanghera, San Clemente, CA (US); Venugopal Allavatam, San Clemente, CA (US)

(73) Assignee: Cameron Health, Inc., St. Paul, MN (US)

( * ) Notice: Subject to any disclaimer, the term of this patent is extended or adjusted under 35 U.S.C. 154(b) by 0 days.

(21) Appl. No.: 13/909,657

(22) Filed: Jun. 4, 2013

(65) Prior Publication Data

US 2013/0324867 A1   Dec. 5, 2013

Related U.S. Application Data

(60) Provisional application No. 61/655,342, filed on Jun. 4, 2012.

(51) Int. Cl.
  *A61B 5/04* (2006.01)
  *A61B 5/00* (2006.01)
  *A61B 5/0452* (2006.01)
  *A61N 1/36* (2006.01)
  *A61B 5/046* (2006.01)

(52) U.S. Cl.
  CPC ............ *A61B 5/04017* (2013.01); *A61B 5/686* (2013.01); *A61B 5/7217* (2013.01); *A61B 5/046* (2013.01); *A61B 5/0452* (2013.01); *A61B 5/7203* (2013.01); *A61N 1/36* (2013.01)
  USPC ........................................................ 600/509

(58) Field of Classification Search
  USPC .......................... 600/509, 483, 510, 515, 516
  See application file for complete search history.

(56) References Cited

U.S. PATENT DOCUMENTS

| | | | |
|---|---|---|---|
| 4,567,900 A | 2/1986 | Moore | |
| 4,603,705 A | 8/1986 | Speicher et al. | |
| 4,693,253 A | 9/1987 | Adams | |
| 4,944,300 A | 7/1990 | Saksena | |
| 5,105,810 A | 4/1992 | Collins et al. | |
| 5,618,287 A | 4/1997 | Fogarty et al. | |
| 6,647,292 B1 | 11/2003 | Bardy et al. | |
| 6,721,597 B1 | 4/2004 | Bardy et al. | |
| 7,149,575 B2 | 12/2006 | Ostroff et al. | |
| 7,248,921 B2 | 7/2007 | Palreddy et al. | |
| 7,330,757 B2 | 2/2008 | Ostroff et al. | |
| 7,623,913 B2 | 11/2009 | Phillips | |
| 7,623,916 B2 | 11/2009 | Julian | |
| 7,655,014 B2 | 2/2010 | Ko et al. | |
| 8,160,686 B2 | 4/2012 | Allavatam et al. | |
| 8,160,687 B2 | 4/2012 | Warren et al. | |
| 2008/0194975 A1* | 8/2008 | MacQuarrie et al. | ......... 600/483 |

(Continued)

*Primary Examiner* — Robert N Wieland
(74) *Attorney, Agent, or Firm* — Schwegman, Lundberg & Woessner, P.A.

(57) ABSTRACT

Implantable cardiac devices and methods of their use. A method of operation in an implantable cardiac device may include steps for characterizing detected events as noise or not noise, identifying a set of consecutive noise events or a threshold quantity of noise events in a set period of time and declaring a noisy series to have occurred. In response to the declaration of a noisy series, the method initiates a baseline correction algorithm. Devices for performing such methods are also disclosed.

19 Claims, 6 Drawing Sheets

(56) References Cited

U.S. PATENT DOCUMENTS

| | | |
|---|---|---|
| 2009/0228057 A1 | 9/2009 | Allavatam et al. |
| 2010/0152799 A1 | 6/2010 | Sanghera et al. |
| 2011/0098775 A1 | 4/2011 | Allavatam et al. |
| 2012/0238892 A1* | 9/2012 | Sarkar .......................... 600/516 |
| 2012/0289845 A1* | 11/2012 | Ghosh et al. .................. 600/510 |
| 2013/0331718 A1* | 12/2013 | Narayan et al. ............... 600/515 |

* cited by examiner

IMPLANTABLE CARDIAC SYSTEMS WITH BASELINE CORRECTION IN RESPONSE TO NOISE DETECTION

CLAIM OF PRIORITY

This patent application claims the benefit under 35 U.S.C. Section 119(e) of U.S. Provisional Patent Application Ser. No. 61/655,342, titled IMPLANTABLE CARDIAC SYSTEMS WITH BASELINE CORRECTION IN RESPONSE TO NOISE DETECTION filed on Jun. 4, 2012, which is incorporated by reference herein in its entirety.

CROSS REFERENCE TO RELATED APPLICATIONS

The present application is related to U.S. patent application Ser. No. 12/636,575, filed Dec. 11, 2009, titled IMPLANTABLE DEFIBRILLATOR SYSTEMS AND METHODS WITH MITIGATIONS FOR SATURATION AVOIDANCE AND ACCOMMODATION, published as US Patent Application Publication No. 2010-0152799, and U.S. Pat. No. 7,623,913, issued Nov. 24, 2009, titled IMPLANTABLE MEDICAL DEVICES USING HEURISTIC FILTERING IN CARDIAC EVENT DETECTION, the disclosures of which are incorporated herein by reference.

BACKGROUND

Implantable cardiac devices include implantable defibrillators, implantable pacemakers, and implantable monitoring devices (and combinations thereof). Such devices monitor the cardiac status of a patient by observation of signals captured with implanted electrodes. Interference with cardiac signal sensing can come from many sources including biological noise (muscle contraction and artifacts of respiration or other movement, for example) and external noise (50/60 Hz line frequency noise, electrical devices, radiofrequency generators, or large magnets, for example). Noise introduced by any of these sources can prevent detection of treatable conditions and/or cause the device to deliver inappropriate therapy. New and alternative ways of detecting and responding to such noise are desired.

SUMMARY

The present invention, in an illustrative embodiment, comprises an implantable cardiac device comprising electrodes for receiving cardiac signals and operational circuitry for processing the cardiac signals received by the electrodes. In the illustrative embodiment, the operational circuitry is configured to perform cardiac event detection on the received signals and, for the detected cardiac events, to perform noise detection. In one example, noise detection is performed by determining turning points in a window associated with a detected event; in other examples, other specific noise detection methods may be used. If a detected event meets selected criteria, it will be used in further analysis of the cardiac signal of a patient in whom the cardiac device is implanted. If a detected event does not meet the selected criteria, it is marked as a noise event. The operational circuitry in the illustrative embodiment is further configured to identify a series of "N" noise events, either consecutive or within a predetermined period of time as a noisy series. If a noisy series occurs, the operational circuitry is further configured to enable a baseline correction method to ensure that the noise that caused the noisy series does not induce a baseline offset and thereby impair sensing. Enablement of the baseline correction method may wait until the noisy series ends. The operational circuitry of the cardiac device may be further configured for additional functionality such as the identification of conditions necessitating therapy delivery such as pacing or defibrillation. In one example, the baseline correction method comprises a dynamic heuristic filter. Other methods of baseline correction can be applied.

The present invention, in another illustrative embodiment, comprises a method of operation in an implantable cardiac device. The illustrative method includes receiving electrical signals from implanted electrodes, detecting events that are likely cardiac events in the received signals, and performing noise detection on the detected events. In the illustrative method, detected events can pass or fail noise detection. The illustrative method further includes observing whether a series of "N" noise events occurs, either consecutively or within a predetermined period of time, and if so, declaring a noisy series has taken place. In the event of a noisy series, the method further comprises enabling a baseline correction method to ensure that the noise that caused the noisy series does not induce a baseline offset and thereby impair sensing. Enablement of the baseline correction method may wait until the noisy series ends. The illustrative method may further include other activity such as the identification of conditions necessitating therapy delivery such as pacing or defibrillation.

In one example, the baseline correction method comprises a dynamic heuristic filter. In another example, the baseline correction method may use adaptive filtering, other filters, etc. In an alternative example, rather than correcting a baseline offset to drive the signal toward the intended quiescent point, the system may modify the manner in which it detects signals to accommodate an identified baseline offset as a way of performing baseline correction.

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives.

As used herein, the term "baseline", in reference to cardiac event detection, refers to the quiescent point of analysis. For example, when there is no signal to detect, the sensed signal returns to its baseline or quiescent point. This is true for either analog or digital signals. Ordinarily, when a cardiac or other signal is sensed, the sensed signal diverges from baseline in proportion to the amplitude of the sensed signal. A "baseline offset" indicates a lasting divergence from the intended baseline/quiescent point of the system, in which the signal is not at "zero" when there is no time-varying signal occurring and remains non-zero for a significant period of time, for example, longer than 500 milliseconds. A baseline offset may also be referred to as a DC offset.

Figure 1:
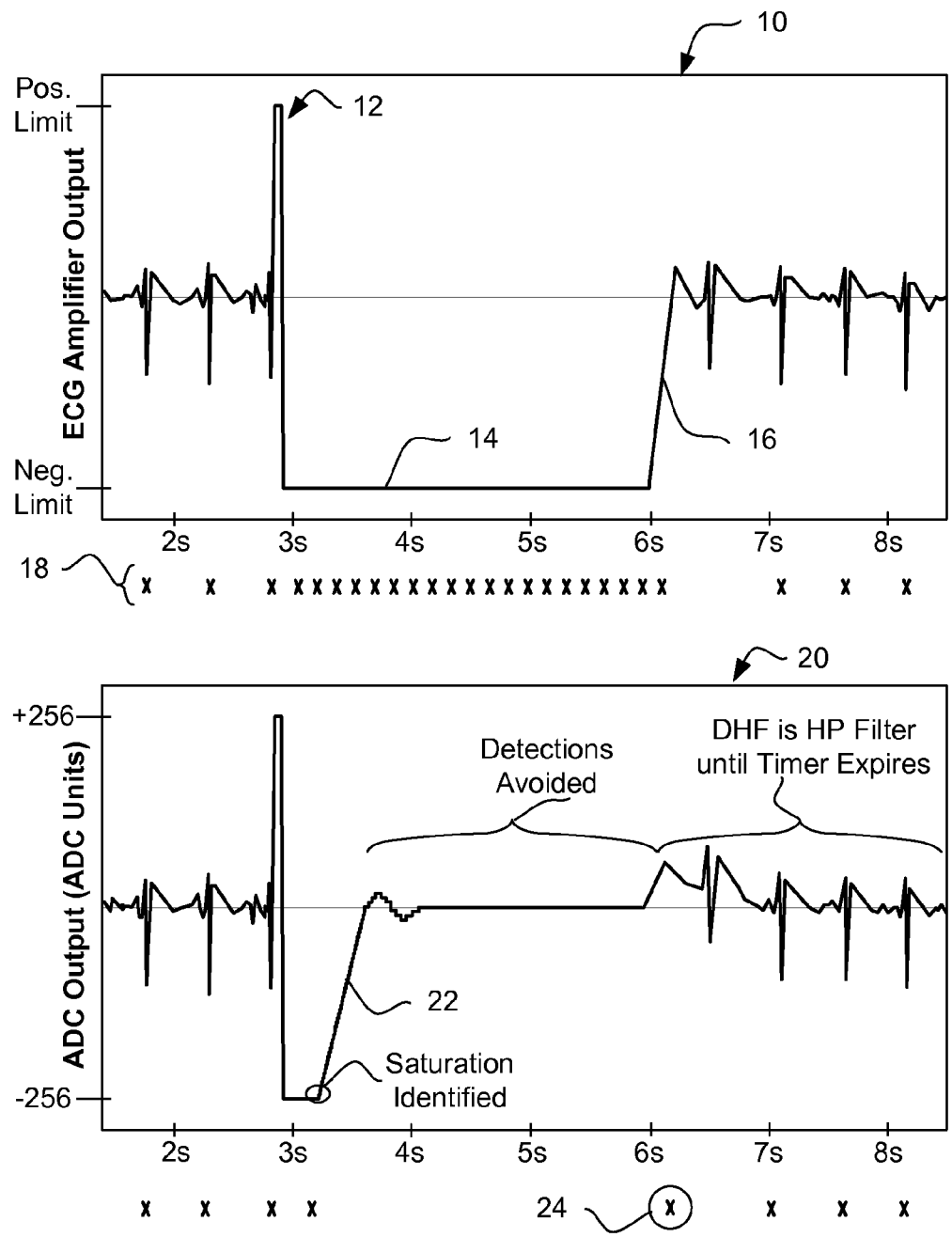
FIG. 1 illustrates graphically the operation of a baseline correction method to prevent overdetection during saturation in an implantable cardiac device.

FIG. 1 illustrates graphically the operation of a baseline correction to prevent overdetection during saturation in an implantable cardiac device. A typical implantable cardiac device will include an amplifier circuit that receives and amplifies the signals captured from implantable electrodes to enable subsequent analysis. In FIG. 1, an illustrative output of an ECG Amplifier Circuit is shown. At point 12, a high voltage pulse appears. In the example, the high voltage pulse is biphasic, as illustrated by the positive excursion which is followed by a negative excursion at 14. The high voltage pulse is sufficiently large to overwhelm the input circuitry, which often includes large DC blocking capacitors which can become charged with an offset by external inputs. The cause of such a high voltage pulse may include external defibrillation or cardioversion or accidental shock, for example. Due to the high amplitude of the pulse, the ECG Amplifier output becomes saturated and, due to the offset introduced in the DC blocking capacitors by the high voltage pulse, the ECG Amplifier remains saturated for several seconds.

This saturation can push the detected signal away from its baseline for up to several seconds. As shown by the "X" markers at 18, numbers "detections" occur during the negative excursion. These detections can lead to inappropriate therapy or charging of high voltage circuitry.

As shown in U.S. patent application Ser. No. 12/636,575, filed Dec. 11, 2009, titled IMPLANTABLE DEFIBRILLATOR SYSTEMS AND METHODS WITH MITIGATIONS FOR SATURATION AVOIDANCE AND ACCOMMODATION, published as US Patent Application Publication No. 2010-0152799, introduction of a large offset 14 that remains static for some period of time can cause very fast detections to occur in the cardiac device and may lead to inappropriate therapy. In the 2010-0152799 publication, saturation rules are provided and a response is defined as shown at 20. Specifically, shortly after the high voltage pulse drives the analog-to-digital converter (ADC) output to its saturation, a dynamic heuristic filter (DHF) method is activated and as shown at 22 the ADC output is returned to baseline. This avoids overdetections during the time of the negative excursion 14. Upon return of the ECG Amplifier Output to its baseline, shown at 16 in the graphic at 10, the DHF continues to operate to keep the signal near baseline and becomes, essentially, a high pass filter. The DHF in this example includes a timer that determines when the DHF becomes inactive.

A detailed explanation of the DHF operation is provided in the 2010-0152799 publication, which is incorporated herein by reference as providing details of implantable cardiac device operation, details of the saturation algorithm disclosed therein, and description of the DHF, among other matters. Another detailed explanation is provided in U.S. Pat. No. 7,623,913, issued Nov. 24, 2009, titled IMPLANTABLE MEDICAL DEVICES USING HEURISTIC FILTERING IN CARDIAC EVENT DETECTION, which is also incorporated herein by reference.

The DHF is one way to implement a baseline correction method. Another baseline correction method may use an adaptive filter. In one method of baseline correction, a one-shot correction can be made by determining an average offset over a period of time or quantity of samples, for example, and adding or subtracting a correction factor. In another example, baseline correction can be managed by modifying the detection features of a system to accommodate the distance of the signal from baseline.

Figure 2:
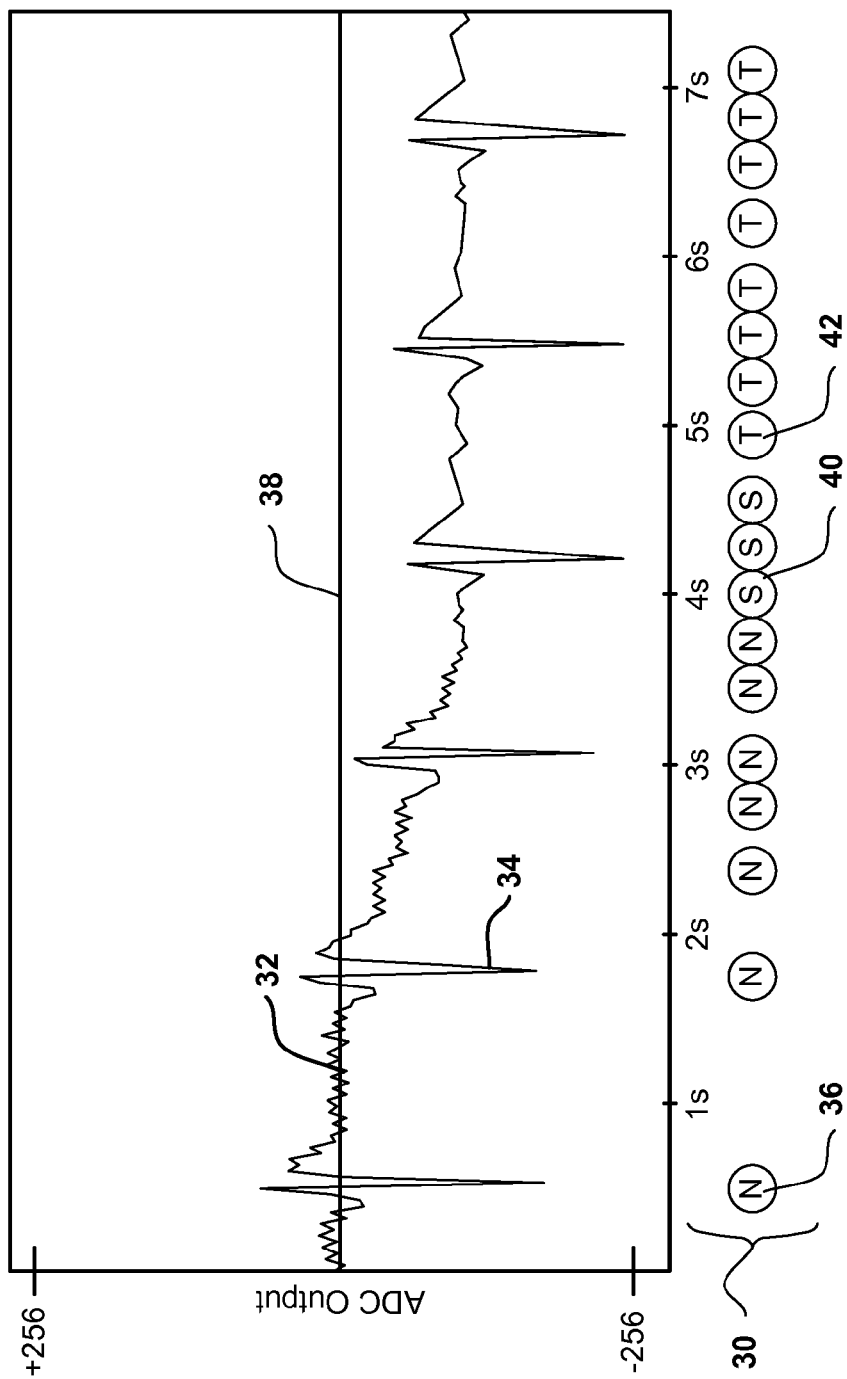
FIG. 2 illustrates the introduction of baseline offset due to an interfering signal on an electrical representation of a cardiac signal.

FIG. 2 illustrates the introduction of baseline offset due to an interfering signal on an electrical representation of a cardiac signal. In this example, the ADC output is shown, and detected events are illustrated by the circled letters at 30, with "N" indicating noise, "S" indicating a normal sensed beat, and "T" indicating a treatable sensed event. In this example, the "T" is applied if the detected rate exceeds a threshold, which is set in the range of about 220 beats per minute. Other detected event classification methods are known. Illustrative examples include U.S. Pat. Nos. 8,160,686 and 8,160,687, each titled METHODS AND DEVICES FOR ACCURATELY CLASSIFYING CARDIAC ACTIVITY, and U.S. Pat. No. 7,330,757, titled METHOD FOR DISCRIMINATING BETWEEN VENTRICULAR AND SUPRAVENTRICULAR ARRHYTHMIAS, each of which is incorporated herein by reference. Other examples are well known to those skilled in the art including numerous commercially available cardiac stimulus systems.

A relatively small amplitude noise signal is shown at 32 as occurring over top of a normal ECG highlighted by R-waves 34. The system is configured to use a detection method to identify likely cardiac events such as that shown in U.S. Pat. No. 8,565,878, titled ACCURATE CARDIAC EVENT DETECTION IN AN IMPLANTABLE CARDIAC STIMULUS DEVICE, the disclosure of which is incorporated herein by reference. Upon event detection, a noise detection algorithm such as the waveform appraisal disclosed in U.S. Pat. No. 7,248,921, titled METHOD AND DEVICES FOR PERFORMING CARDIAC WAVEFORM APPRAISAL, as well as U.S. patent application Ser. No. 12/913,647, titled ADAPTIVE WAVEFORM APPRAISAL IN AN IMPLANTABLE CARDIAC SYSTEM, and published as US Patent Application Publication Number 2011-0098775, the disclosures of which are incorporated herein by reference. Other noise detection methods may be used instead.

As is well understood in the art, noise signals can have unpredictable effects on a sensing architecture. In the illustrative example shown in FIG. 2, the ADC Output drifts away from the baseline 38, due to the noise signal. While the noise persists, detected events are marked as noise 36. Once identified as noise, those detections can be discarded, ignored, or may cause a device to institute methods to inhibit therapy, using methods well known in the art. However, as shown at 40, once the noise stops, the detected events are no longer marked as noise. Even though the noise stopped, an offset persists.

In a typical system, the DC blocking filters often have a response in the range of a few hertz. As a result the offset can be corrected in a few seconds. However, the detection methods used in cardiac systems are set up to detect signals very quickly to correctly identify arrhythmias in ranges over 200 beats-per-minute. As a result, the detect events start occurring very quickly as shown at 40, and the system begins marking treatable beats at 42. FIG. 1 also shows this rapid detection occurring at 18.

Depending upon the time it takes for recovery to occur, which is itself dependent on the size of the offset, the series of treatable event classifications that begins at 42 may lead the device to begin preparing for therapy delivery. Such preparations are a waste of energy as the therapy is not needed. If the offset does not correct in time, this sequence may lead to inappropriate therapy which can be harmful to the patient in addition to shortening device life.

One of the difficulties with the event depicted in FIG. 2 is that the signal is not saturated, as it was in FIG. 1. As a result, a saturation detection method may not function. Looking for a single-sided signal may yield another way to identify the offset. However, though not shown in FIG. 2, a small offset can leave the signal biphasic. In addition to noise, other challenging inputs signals may create an offset, depending upon the detection architecture. For example, if received signals exceed the dynamic range of input circuitry, or if the maximum slew rate of the system is exceeded, the ADC circuitry may not keep up with the analog signal even without saturating the digital domain.

Figure 3:
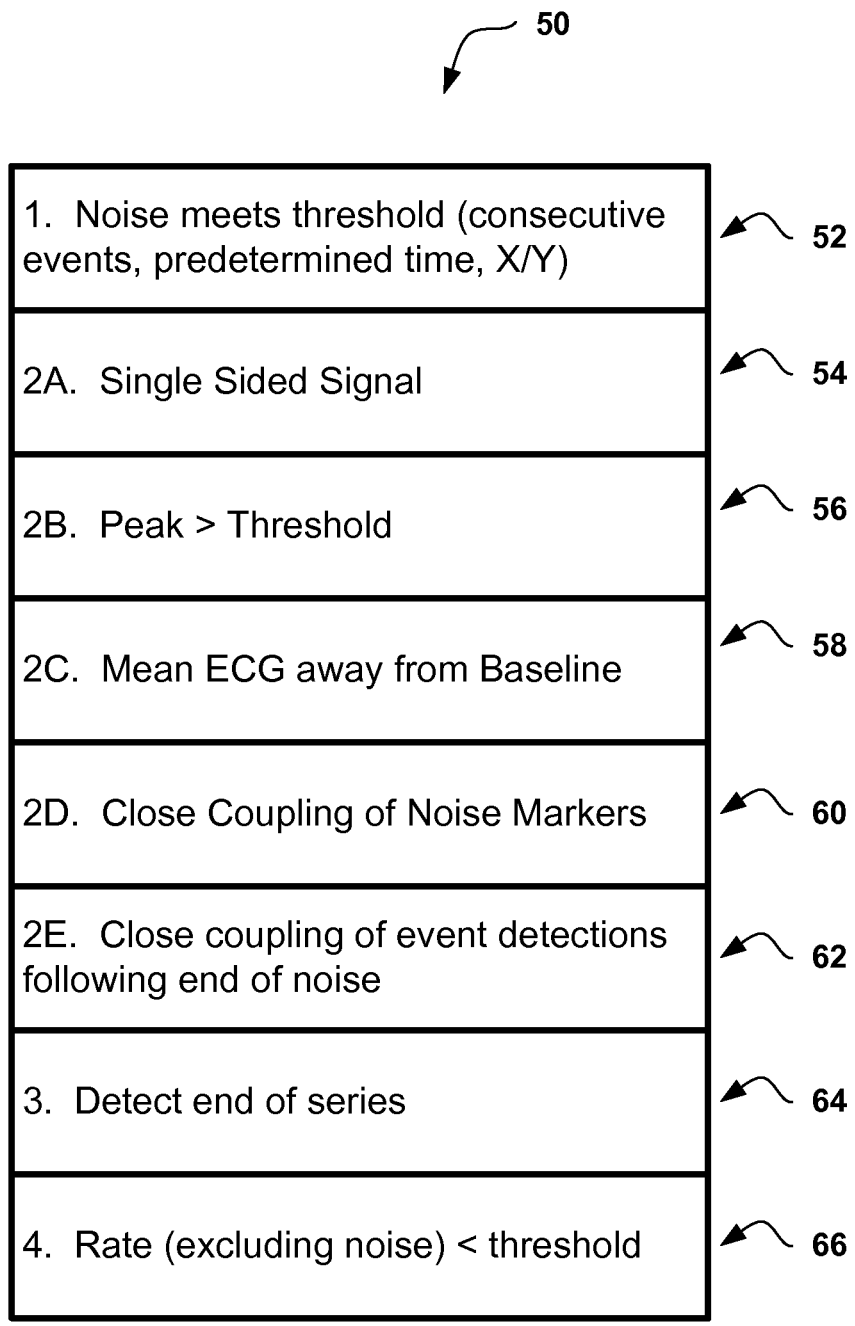
FIG. 3 shows illustrative rules for an example.

FIG. 3 shows illustrative rules for an example response to the issue shown in FIG. 2. Several rules are shown at 50. In an illustrative example, a first rule checks for the existence of "N" noise markers, as shown at 52. The noise marker rule may call for consecutive markers or may call for a quantity of such markers to occur in a fixed period of time. For example, a consecutive rule approach may look for between four and ten noise markers in a row. A fixed period of time rule may require between four to ten noise markers in a set period of time such as two to four seconds (i.e. four noise markers in two seconds, up to ten noise markers in four seconds). A combined rule may look for four to ten noise markers in two to four seconds. One example calls for five consecutive noise markers occurring within two seconds. In another example, any number of noise events, such as 1 or more, may meet the requirement at 1. In a further example, an X/Y rule may be used, such as ⅗ recent detected events being called "noisy", or some other ratio.

Several alternatives are provided for optional additional rules. In one example, 2A, a second rule calls for a single sided signal, that is, a signal that does not cross baseline, as shown at 54. In another example, 2B, a second rule calls for a signal peak to be greater than a predefined threshold, such as 80% of the dynamic range of the system or 80% of the maximum ADC range, as shown at 56. In another example, 2C, the mean ECG, calculated over a fixed period of time or quantity of samples such as a one second window, must be away from the baseline by at least some threshold, such as 10% of the dynamic range of the system or 10% of the maximum ADC range, as shown at 58. In another example, the noise markers may require close coupling, for example, out of the N consecutive markers, at least two noise events would have to occur within some set period of time, for example, two noise markers less than 400 ms apart. Another example, 2E, looks for close coupling of event detections following the end of the noise series, as shown at 62; the standard applied at 2E may look for event detection couplings that occur so fast that cardiac origin is deemed unlikely, for example, >300 bpm, for a series of consecutive intervals.

Any one or all of rules 2A-2E may be omitted. In one example, the rules are alternatives to one another, such that meeting rule 1 and any of rules 2A-2E would allow the device to declare that a noisy series has taken place. Rule 1 may be used standing alone to declare that a noisy series has occurred.

As shown at 64, an additional rule may be applied calling for detection of the end of the series before declaring that a noisy series has occurred. For example, if a series of consecutive noise markers is required, then at least one non-noise marker may be required to call the rule set 50 fully met. This would ensure that the responsive mechanism (in several examples, a baseline correction method) does not trigger until the noise stops. If the baseline correction triggers early, while the noise is ongoing, it may have to remain on for a longer period of time than necessary.

Another (optional) rule may check that the detected rate, excluding noise markers, is below a threshold, as indicated at 66. This additional rule may be prevent the activation of the baseline offset response during potential tachyarrhythmias, when it could have the potential to delay therapy delivery by modifying the sensed signal unnecessarily.

Figure 4:
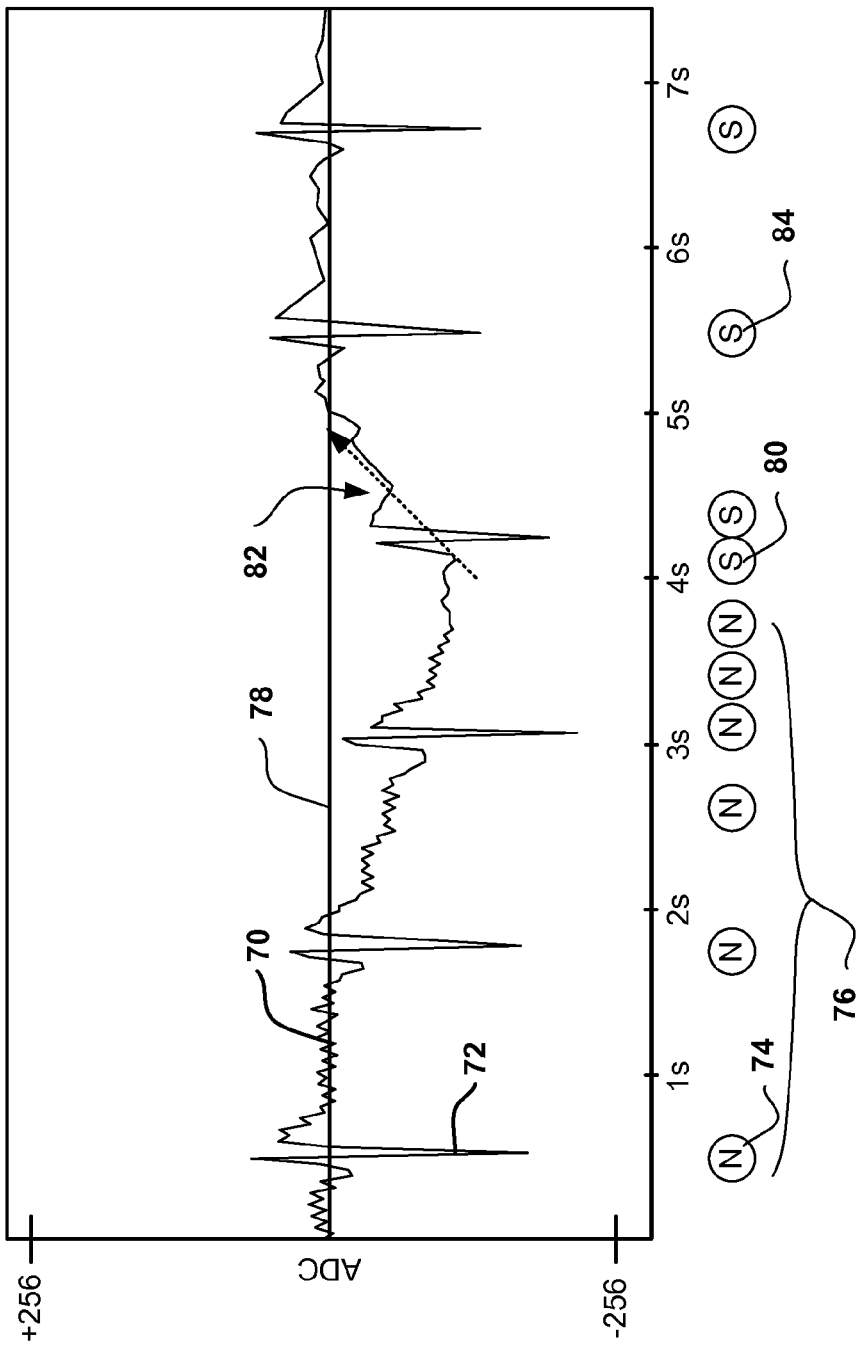
FIG. 4 illustrates the operation of a method to correct the baseline offset and overdetection shown by FIG. 2.

FIG. 4 illustrates the operation of a method to correct the baseline offset and overdetection shown by FIG. 2. In this example, again, the signal includes noise illustrated at 70 and R-wave peaks 72 that are readily discerned. The system generates noise markers 74 in response to the noise 70. As shown at 76, noise detections occur rapidly as the signal drifts away from the baseline 78. The noise then stops as shown at 80. During the period shown at 76, a number of consecutive noise markers occur (here, five consecutive markers were needed), meeting rule 1 of FIG. 3.

As noted, rule 1 may be applied by itself. Optional rules 2A-2E (FIG. 3) may also be applied, and each of those may be met, depending on the particularities of their application, in the example of FIG. 4. For example, the signals for each of the detected noise events after the 2 s mark are single sided and do not cross the baseline 78, meeting optional rule 2A, if that were being applied. The peak of the R-wave at 3 s exceeds 80% of the ADC limit (−256), meeting optional rule 2B if that were being applied. The mean of the signal has drifted away from the baseline during the time period from 3 s to 4 s in FIG. 4, which would meet optional rule 2C, if that were being applied. The last four of those noise markers occur in less than two seconds, which would meet optional rule 2D if that were being applied.

As shown at 80, a sensed event occurs after the noise 76 stops. This would meet rule 3 from FIG. 3, showing that the noise has stopped or abated sufficiently to allow a normal sensed event to occur. As noted, again, rule 3 from FIG. 3 is optional and may be omitted. The first two sensed events following the end of the noise are very closely coupled, which could meet optional rule 2E from FIG. 3 if that were being applied.

In the illustrative sequence shown in FIG. 4, the baseline correction method is applied after the detection at 80. As illustrated at 82, the signal mean is quickly pushed down to the baseline. A DHF, as described in US Patent Application Publication No. 2010-0152799, titled IMPLANTABLE DEFIBRILLATOR SYSTEMS AND METHODS WITH MITIGATIONS FOR SATURATION AVOIDANCE AND ACCOMMODATION, and U.S. Pat. No. 7,623,913, titled IMPLANTABLE MEDICAL DEVICES USING HEURISTIC FILTERING IN CARDIAC EVENT DETECTION, may be used as the baseline correction method.

Briefly, the DHF can operate by adjusting the ADC output by one or more steps in a direction towards the baseline by calculating an average ADC output over a fixed period of time or quantity of samples, with the adjustments occurring at intervals. What makes the DHF dynamic is the ability to modify the intervals at which adjustments occur to account for the measured distance from the baseline of the ADC output. In one embodiment, the ADC is adjusted using a heuristic filter (16 Hz in one example) at a fixed frequency all of the time, providing proportional feedback to the ADC itself in the form of a high pass filter. When the DHF is activated, the fixed frequency is replaced with a variable frequency (from 16 Hz up to 1024 Hz by powers of two), starting at 1024 Hz and reducing the variable frequency when the averaged ADC output gets closer to the baseline. Higher or lower (or simply different) rates may be used.

Other baseline correction methods may be applied. In one example, an additional high pass filter may be applied in response to identification of the noise series, in either the digital domain (such as through modification of digital filtering coefficients) or in the analog domain (such as by routing signal through an additional high pass filter). In another example, a step correction can be applied by observing an averaged signal over a large block of time (such as one to five seconds, for example), and then subtracting the averaged signal from the sensed signal. Subtraction could be applied in the analog domain by manipulation of a stored voltage on an analog filtering capacitor (i.e. a "recharge step"—see U.S. Pat. No. 7,623,916, titled IMPLANTABLE CARDIAC STIMULUS DEVICES AND METHODS WITH INPUT RECHARGE CIRCUITRY, the disclosure of which is incorporated herein by reference). Subtraction could also be applied in the digital domain by adding an offset to the digital output of the analog-to-digital convertor (ADC) or by manipulating the ADC itself.

As a result of the baseline correction method illustrated at 82, by the 5 s point in the drawing, the signal is promptly returned to its baseline, and normal sensing resumes as shown at 84. No series of treatable event markers appears because the detected rate, excluding the noise events at 76, remains relatively low. This approach can avoid unnecessary charging and inappropriate therapy.

Figure 5:
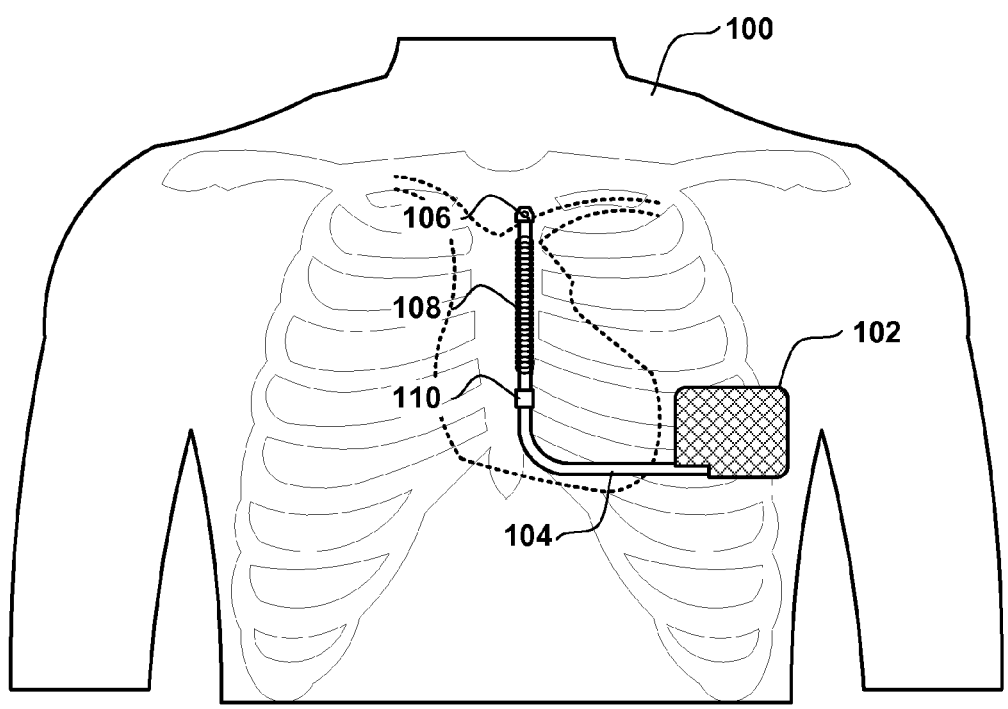
FIG. 5 shows an illustrative implantable cardiac device in the form of a subcutaneous defibrillator.

FIG. 5 shows an illustrative implantable cardiac device in the form of a subcutaneous defibrillator relative to the anatomy of an implantee 100. The illustrative implant is subcutaneous-only, and there is no electrode or lead assembly in or in contact with the heart or heart tissue, and no lead assembly or other component residing in the vasculature. Instead, the illustrative system includes a canister 102 attached to a lead 104, and both are disposed subcutaneously, between the ribcage and the skin of the patient 100.

In the illustration of FIG. 5, the canister 102 is disposed near the midaxillary line of the patient, at about the level of the cardiac apex and the inframammary crease. The lead 104 extends in a medial direction to approximately the xiphoid and then toward the head of the patient along the sternum, terminating near the top of the sternum. In an alternative embodiment, one or more leads may be placed in or on the heart. The canister 102 may have one or several electrodes. A lead may be omitted, with the canister having all needed electrodes thereon, if desired. Other designs may be used with the present invention including, and without limitation, transvenous systems, intravascular systems, epicardial systems, and systems having combinations of one or more of subcutaneous, transvascular, epicardial leads, active canisters, and/or multiple canister electrodes.

The lead 104 includes a distal sensing electrode 106, a therapy delivery coil 108 and a proximal sensing electrode 110. ("Distal" and "Proximal" refer to position along the lead 104, with the distal electrode 106 being farthest from the connection to the canister 102). The distal sensing electrode 106 may, as shown, include a suture hole useful for securing the lead 104 to subcutaneous tissue upon implantation.

If desired, the therapy delivery coil 108 may be used as a sensing electrode, and one or more of the sensing electrodes 106, 110 may also be used as therapy delivery electrodes. Different arrangements of the electrodes (distal tip as coil, multiple sense electrodes distal of the coil, and/or additional proximal electrodes) may be used, and the electrode designs shown are merely illustrative. The canister 102 may also include one or more suture features (such as suture holes in the header) for securing to subcutaneous tissue. In some examples, a suture sleeve is provided on the lead 104, for example, near the xiphoid, to provide an additional point of fixation or as a substitute for the suture hole on the distal electrode 106. Multiple leads may be provided, if desired.

The lead 104 may include multiple separate conductors for the several electrodes 106, 108, 110 and the lead 104 may be described as a lead electrode assembly, without limiting lead 104 to any particular internal structure or manner of construction. This example is merely illustrative. Additional implantation locations are shown, for example, in commonly owned U.S. Pat. No. 7,655,014, titled APPARATUS AND METHOD FOR SUBCUTANEOUS ELECTRODE INSERTION, and/or U.S. Pat. Nos. 6,647,292, 6,721,597 and 7,149,575; any of the implantation locations shown in these patents and applications may be used as well. In one example, a system having the three-electrode lead 104 and active canister 102 as shown in FIG. 5 is implanted with the active canister 102 disposed approximately anterior of the left axilla with the lead 104 extending past the axilla to a location over the posterior region of the ribs of the patient, with the distal end of the lead to the left of the spine of the patient, creating an anterior-posterior shock or sense vector between the active canister 102 and the coil electrode 108. The '292 patent includes certain unitary embodiments, which may also be used, as desired. Epicardial or transvenous systems are shown, for example, in U.S. Pat. Nos. 4,603,705, 4,693,253, 4,944,300, 5,105,810, 4,567,900 and/or 5,618,287. Other locations, systems and combinations may be used.

The system may include operational circuitry having any suitable components for detection and control (such as an input ECG amplifier, filtering circuitry, analog-to-digital conversion circuitry, memory, a microcontroller, etc.), telemetry (such as an antenna, amplifier, mixer, transceiver, etc.), power supply (any suitable battery technology may be used; lithium chemistries are common in the art) and output circuitry (such as switches, high-power capacitors, and charging circuitry). Any suitable materials may be used for the lead 104 and canister 102. An illustrative example includes a titanium canister 102 having a titanium nitride coating, a polyurethane body for the lead 104 with a silicone sheath thereon, and MP35N conductors in the lead 104 and electrodes 106, 108, 110. Various other materials are known in the art and may be substituted for any of these items. Illustrative additional or alternative design details include iridium oxide or porous carbon coatings, platinum or silver electrodes, conductors and/or canister materials, and other materials for the body of lead 104. Drawn filled tubes are known for the conductors as well. Other structures and components may be used; those noted here are for illustrative purposes only and the invention is not limited to these particular examples.

Various alternatives and details for these designs, materials and implantation approaches are known to those skilled in the art. Commercially available systems in which the above methods can be performed or which may be configured to perform such methods are known including the Boston Scientific Teligen® ICD and S-ICD® System, Medtronic Concerto® and Virtuoso® systems, and St. Jude Medical Promote® RF and Current® RF systems. Such platforms include numerous examples and alternatives for the operational circuitry, battery, canister, lead, and other system elements.

Figure 6:
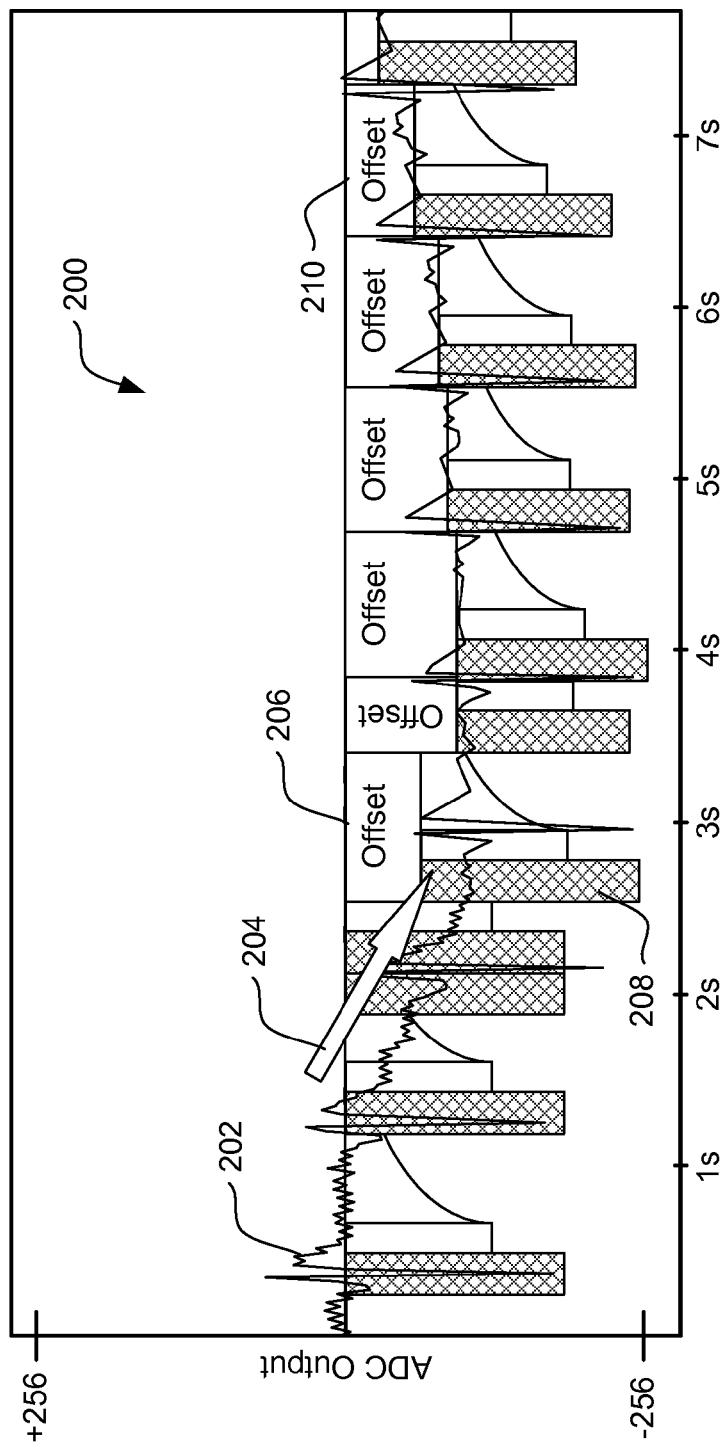
FIG. 6 illustrates another method of avoiding overdetection due to shifting of the baseline by including an offset in the detection profile.

FIG. 6 illustrates another method of avoiding overdetection due to shifting of the baseline by including an offset in the detection profile. In the example, at 200, the ADC output of a device is shown tracking the ECG of a patient. As shown at 202, the ECG is choppy, indicating some noise signal is overlaid on the signal. This causes a drift over time as shown at 204 from the baseline, which can occur, for example, if there is an imbalance in components or calculations, or if the slew rate of dynamic range of the input is exceeded, for example.

In the illustrative method, an average magnitude of the ECG is calculated repeatedly. The average magnitude will normally remain at or near the quiescent point, which is at zero in ADC counts in the example shown in FIG. 6. The average magnitude can be calculated for a relatively long period of time, in the range of 500 milliseconds out to three or more seconds. In one example, magnitude is calculated using at least a second of data. The long period would avoid determining the average magnitude for a partial cardiac cycle, which could throw the calculation off insofar as the goal in this example is to determine how closely the quiescent point is being tracked.

If the average magnitude deviates from the quiescent point, this may indicate that the signal has drifted as shown at 204. In some embodiments, some relatively small about of drift is expected, and so a threshold may be applied to determine a minimum amount of deviation that could trigger a response. For example, a threshold may be set so that a drift of five percent or less of the ADC may be ignored. Other thresholds can be used.

Rather than correction by adjusting the signal average using a dynamic heuristic as shown above, the example in FIG. 6 uses an offset approach. The offset can be calculated by taking a percentage of the average signal over a predefined period of time. The predefined period of time may be the same as the period used to determine whether the average magnitude has deviated, if desired. In other embodiments, the offset is calculated using a different period of time which may be shorter. For example, the offset can be calculated using an average magnitude across a half-second (500 ms) of time, while the deviation of the average magnitude can be calculated using one to three seconds of time.

The offset 206 is added to the detection profile 208. The offset 206 allows the detection profile 208 to be applied as if the baseline was nearer to the actual average magnitude than is in fact the case. This avoids overdetection by reducing the effective amplitude of the detected signal relative to the detection profile 208. As time passes, the signal gradually returns to baseline using the ordinary proportional and integral feedback loop of the system, which can be implemented using an ADC average output correction, or by applying DC filtering in the analog domain, among other operations. Thus the offset, as shown at 210, becomes smaller over time. Once the offset is calculated to a level that is below a threshold, the offset may cease to be used.

In another alternative, an offset may be "always on", such that the average magnitude is not used to trigger a different operation. Instead, the offset may be calculated each time the detection profile is applied to the signal. In another embodiment, the offset capability can be enabled in the manners discussed above for enabling the baseline correction, such as in response to a series of noise detections, to a number of noise detection during a particular period of time, or to observing a minimum quantity of noise detections out of a set of detected events. At a high level, the prior art implantable cardiac device typically responds to the identification of noise by implementing a blanking period. During blanking, the implantable cardiac device is essentially blind to anything that is occurring. Some alternatives have discussed extending a refractory period following detection of a single event if noise is observed as well. During refractory, the system is not blind like in blanking, but is not able to declare the onset of a second cardiac event. Either way, undersensing of the cardiac signal is deemed acceptable in such systems in view of the observation of noise.

In the present invention, however, the implantable system does not necessarily have to enter a blanking or extended refractory period when noise is identified, although such additional mitigations may be used in conjunction with the present invention. Generally speaking, upon identification of a condition that could cause an offset, including noise, the present invention allows a triggered response to ensure baseline recovery/management. In some examples, this is done via the dynamic heuristic filter or other baseline restoration process. High pass filtering may be used. In another example shown above, the detection profile used in sensing cardiac events can be offset to accommodate drifting away from the baseline.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the claims, along with the full scope of equivalents to which such claims are entitled.

The claimed invention is:

1. An implantable cardiac device comprising electrodes for receiving cardiac signals and operational circuitry for processing the cardiac signals received by the electrodes; in which the operational circuitry is configured to:
   receive signals via the electrodes;
   detect events in the received signals by comparing the received signals to one or more thresholds and identifying threshold crossings;
   determine which, if any, of the detected events are noisy;
   determine whether a noise condition has been detected; and
   if a noise condition has been detected, enable a baseline correction method to ensure that the noise that caused the noise condition does not induce a baseline offset and thereby impair sensing.

2. The implantable cardiac device of claim 1 wherein the operational circuitry is configured to determine whether each detected event is noisy by:
   determining how many turning points occur in a window associated with a detected event; and
   comparing the quantity of such turning points to a threshold;
   wherein the operational circuitry is configured to determine that a given detected event is noisy if the quantity of turning points in the window for the given detected event exceeds the threshold.

3. The implantable cardiac device of claim 1 wherein the baseline correction method comprises operation of a dynamic heuristic filter.

4. The implantable cardiac device of claim 1 wherein the operational circuitry is configured to enable the baseline correction method for a set period of time.

5. The implantable cardiac device of claim 1 wherein the operational circuitry is configured to perform the baseline correction method by setting an initial dynamic adjustment period and performing each of the following steps several times:
   a) repeatedly performing a sensing baseline adjustment protocol at intervals defined by the dynamic adjustment period; and
   b) observing a distance between the sensing baseline and a desired quiescent point and modifying the dynamic adjustment period in response to the observed distance between the sensing baseline and desired quiescent point.

6. The implantable cardiac device of claim 1 wherein the operational circuitry is configured to determine whether a noise condition has been detected by observing whether a predefined quantity of consecutive noisy events has occurred.

7. The implantable cardiac device of claim 1 wherein the operational circuitry is configured to determine whether a noise condition has been detected by observing whether a predefined number of noisy events have occurred in a set period of time.

8. The implantable cardiac device of claim 1 wherein the operational circuitry is configured to determine whether a noise condition has been detected by observing whether a predefined number of noisy events have occurred in a predefined quantity of detected events.

9. A method of operation in an implantable cardiac device that includes electrodes for receiving cardiac signals and operational circuitry for processing the cardiac signals received by the electrodes; the method comprising:
   the operational circuitry receiving signals via the electrodes;
   the operational circuitry detecting events in the received signals by comparing the received signals to one or more thresholds and identifying threshold crossings;
   the operational circuitry determining which, if any, of the detected events are noisy;
   the operational circuitry determining whether a noise condition has been detected; and
   if a noise condition has been detected, the operational circuitry enabling a baseline correction method to ensure that the noise that caused the noise condition does not induce a baseline offset and thereby impair sensing.

10. The method of claim 9 wherein the step of determining whether each detected event is noisy is performed by:
    determining how many turning points occur in a window associated with a detected event; and
    comparing the quantity of such turning points to a threshold;
    wherein a given detected event is determined to be noisy if the quantity of turning points in the window for the given detected event exceeds the threshold.

11. The method of claim 9 wherein the baseline correction method includes operation of a dynamic heuristic filter.

12. The method of claim 9 wherein the operational circuitry is configured to enable the baseline correction method for a set period of time.

13. The method of claim 9 wherein the baseline correction method includes setting an initial dynamic adjustment period and performing each of the following steps several times:
    a) repeatedly performing a sensing baseline adjustment protocol at intervals defined by the dynamic adjustment period; and
    b) observing a distance between the sensing baseline and a desired quiescent point and modifying the dynamic adjustment period in response to the observed distance between the sensing baseline and desired quiescent point.

14. The method of claim 9 wherein the step of determining whether a noise condition has been detected is performed by observing whether a predefined quantity of consecutive noisy events has occurred.

15. The method of claim 9 wherein determining whether a noise condition has been detected is performed by observing whether a predefined number of noisy events have occurred in a set period of time.

16. The method of claim 9 wherein determining whether a noise condition has been detected is performed by observing whether a predefined number of noisy events have occurred in a predefined quantity of detected events.

17. An implantable cardiac device comprising electrodes for receiving cardiac signals and operational circuitry for processing the cardiac signals received by the electrodes; in which the operational circuitry is configured to:

receive signals via the electrodes;

detect events in the received signals by comparing the received signals to one or more detection thresholds and identifying detection threshold crossings;

identify an average magnitude for the received signals wherein average magnitude is determined by sampling the received signals across a period of time that exceeds a single cardiac cycle;

determine whether the average magnitude deviates from a quiescent point;

adjust the detection threshold using a correction factor related to the deviation of the average magnitude from the quiescent point; and detect at least one cardiac event using the detection threshold as adjusted by the correction factor.

18. The implantable cardiac device as in claim 17 wherein the average magnitude is determined by sampling at least one second of cardiac signal.

19. The implantable cardiac device as in claim 17 wherein the operational circuitry is configured to determine that the average magnitude deviates from the quiescent point by determining if the average magnitude is different from the quiescent point by at least a predetermined amount.

\* \* \* \* \*